(12) United States Patent
Bergey

(10) Patent No.: US 12,128,177 B2
(45) Date of Patent: Oct. 29, 2024

(54) BLISTER PACKAGE FOR PHARMACEUTICAL CARTRIDGES

(71) Applicant: MannKind Corporation, Westlake Village, CA (US)

(72) Inventor: Michael S. Bergey, Newtown, PA (US)

(73) Assignee: MannKind Corporation, Danbury, CT (US)

( * ) Notice: Subject to any disclaimer, the term of this patent is extended or adjusted under 35 U.S.C. 154(b) by 407 days.

(21) Appl. No.: 16/847,483

(22) Filed: Apr. 13, 2020

(65) Prior Publication Data

US 2020/0238026 A1    Jul. 30, 2020

Related U.S. Application Data

(62) Division of application No. 14/559,735, filed on Dec. 3, 2014, now Pat. No. 10,625,034, which is a division of application No. 13/436,698, filed on Mar. 30, 2012, now Pat. No. 8,925,726.

(60) Provisional application No. 61/470,982, filed on Apr. 1, 2011.

(51) Int. Cl.
| | | |
|---|---|---|
| *A61M 15/00* | (2006.01) | |
| *B29C 51/14* | (2006.01) | |
| *B65B 9/04* | (2006.01) | |
| *B65B 47/02* | (2006.01) | |
| *B65B 51/10* | (2006.01) | |
| *B65D 75/32* | (2006.01) | |
| *A61J 1/03* | (2023.01) | |
| *B29K 27/06* | (2006.01) | |
| *B29K 27/12* | (2006.01) | |
| *B29K 105/00* | (2006.01) | |
| *B29L 9/00* | (2006.01) | |
| *B29L 31/00* | (2006.01) | |
| *B65B 11/52* | (2006.01) | |
| *B65D 6/00* | (2006.01) | |
| *B65D 83/04* | (2006.01) | |

(52) U.S. Cl.
CPC ......... *A61M 15/0048* (2014.02); *B29C 51/14* (2013.01); *B65B 9/045* (2013.01); *B65B 47/02* (2013.01); *B65B 51/10* (2013.01); *B65D 75/327* (2013.01); *A61J 1/035* (2013.01); *A61M 15/0045* (2013.01); *A61M 15/0065* (2013.01); *A61M 2207/00* (2013.01); *B29K 2027/06* (2013.01); *B29K 2027/12* (2013.01); *B29K 2105/256* (2013.01); *B29L 2009/00* (2013.01); *B29L 2031/712* (2013.01); *B65B 11/52* (2013.01); *B65B 2220/14* (2013.01); *B65D 11/20* (2013.01); *B65D 83/0463* (2013.01)

(58) Field of Classification Search
CPC ..... B65B 47/02; B65B 9/045; B65D 83/0463; B29C 51/14
USPC .......................................................... 53/453
See application file for complete search history.

(56) References Cited

U.S. PATENT DOCUMENTS 4,786,534 A * 11/1988 Aiken ................ A45D 40/0087
206/823
4,962,856 A * 10/1990 Carter .................... B65D 75/36
206/439

(Continued)

*Primary Examiner* — Robert F Long
*Assistant Examiner* — Xavier A Madison
(74) *Attorney, Agent, or Firm* — K&L Gates LLP; Louis C. Cullman; Hal Gibson

(57) ABSTRACT

A blister packaging for a pharmaceutical cartridge or capsule and methods of forming same are disclosed.

15 Claims, 11 Drawing Sheets

(56) References Cited

U.S. PATENT DOCUMENTS

| | | | | |
|---|---|---|---|---|
| 5,052,558 | A * | 10/1991 | Carter | B65D 75/326 |
| | | | | 206/439 |
| 5,390,792 | A * | 2/1995 | Van Ness | A61L 2/26 |
| | | | | 206/439 |
| 5,485,917 | A * | 1/1996 | Early | A61B 50/30 |
| | | | | 206/363 |
| 5,830,547 | A * | 11/1998 | MacKenzie | B32B 27/30 |
| | | | | 428/36.1 |
| 5,842,326 | A * | 12/1998 | Wolf | B65B 55/10 |
| | | | | 422/26 |
| 6,050,400 | A * | 4/2000 | Taskis | B65D 81/266 |
| | | | | 206/467 |
| 6,155,423 | A * | 12/2000 | Katzner | B65D 75/327 |
| | | | | 206/534 |
| 6,409,019 | B1 * | 6/2002 | Hornsby | B65D 75/36 |
| | | | | 206/483 |
| 8,424,518 | B2 * | 4/2013 | Smutney | A61K 31/495 |
| | | | | 128/203.15 |
| 8,806,842 | B1 * | 8/2014 | Penn | B65D 75/5811 |
| | | | | 53/474 |
| 8,925,726 | B2 * | 1/2015 | Bergey | B65B 51/10 |
| | | | | 206/532 |
| 11,511,923 | B2 * | 11/2022 | Bhalla | B65D 75/327 |
| 2010/0181008 | A1 * | 7/2010 | Tang | B29C 44/08 |
| | | | | 156/78 |
| 2011/0036736 | A1 * | 2/2011 | Knowlton | A61B 50/33 |
| | | | | 156/224 |
| 2015/0368018 | A1 * | 12/2015 | Broedsgaard | B65D 75/367 |
| | | | | 53/478 |
| 2017/0137159 | A1 * | 5/2017 | Sullivan | B32B 15/09 |
| 2017/0247128 | A1 * | 8/2017 | Klocke | B65B 3/022 |
| 2018/0162617 | A1 * | 6/2018 | Popkin | B65D 75/566 |

\* cited by examiner

FIG. 10
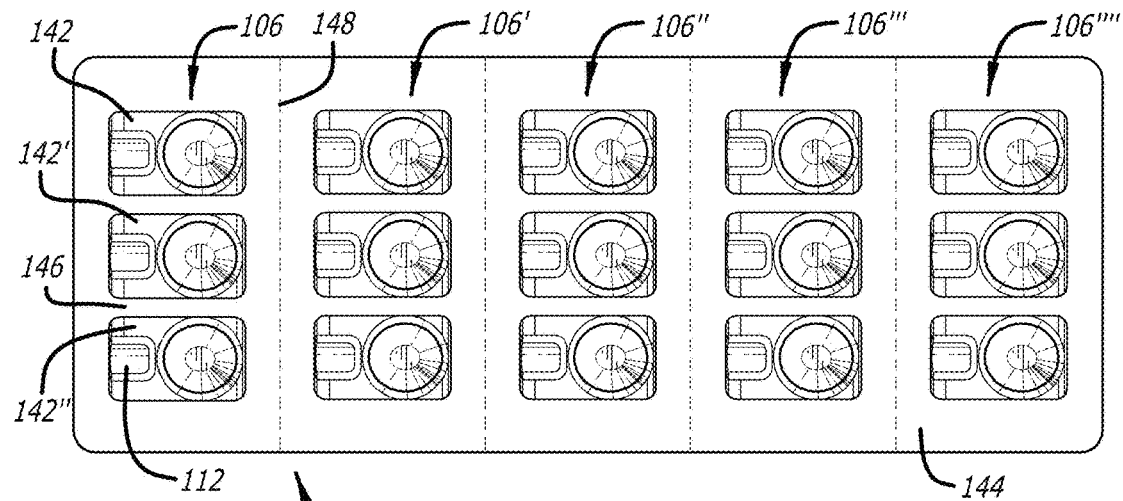
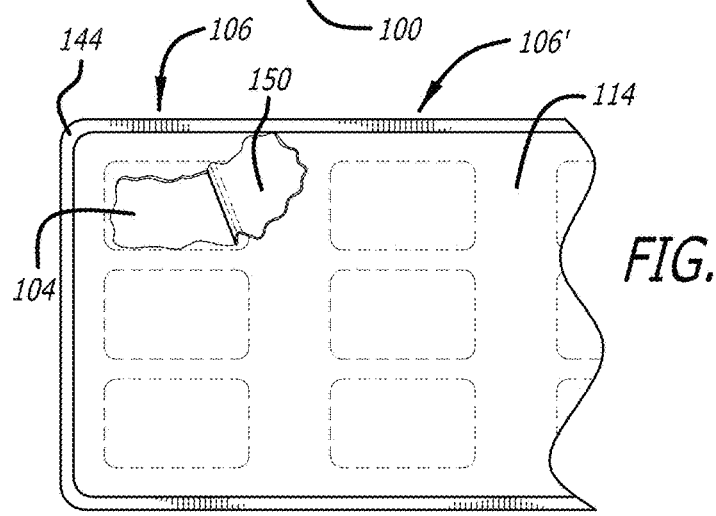
FIG. 11A
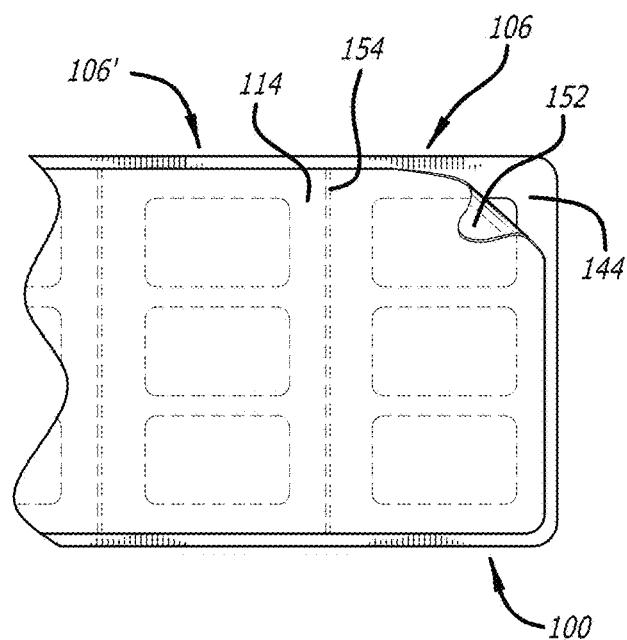
FIG. 11B

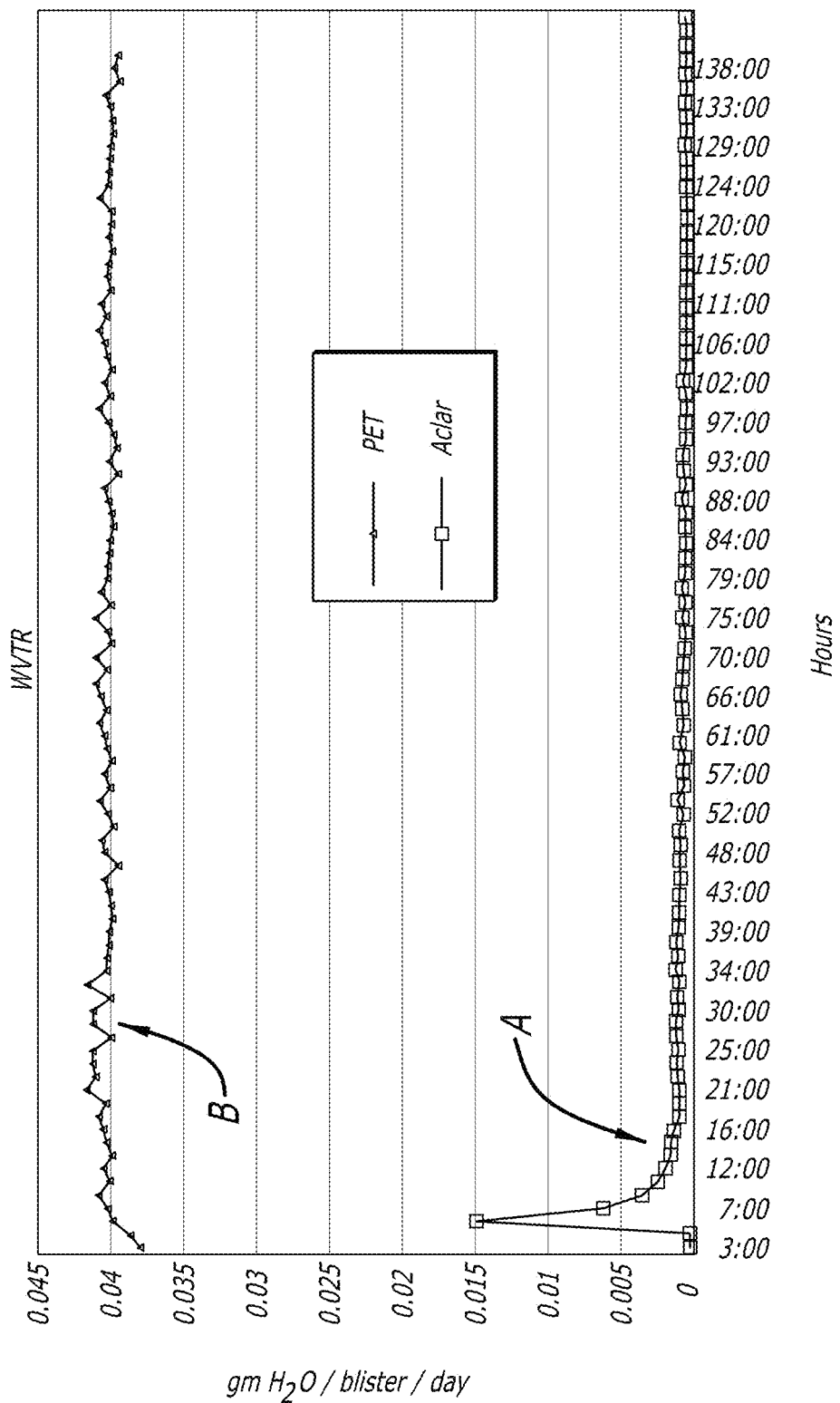

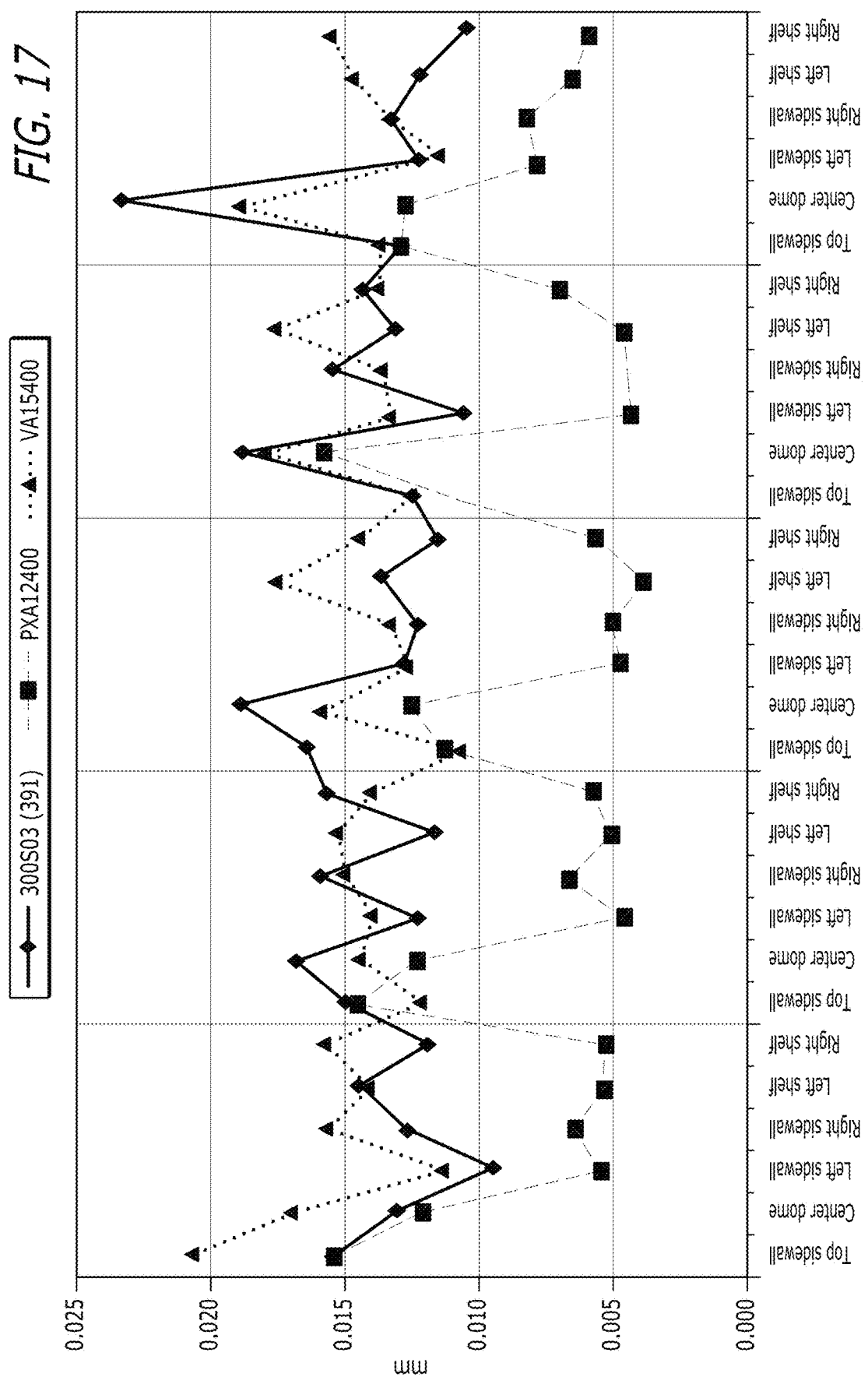

BLISTER PACKAGE FOR PHARMACEUTICAL CARTRIDGES

CROSS REFERENCE TO RELATED APPLICATIONS

This application is a divisional application of U.S. patent application Ser. No. 14/559,735, filed Dec. 3, 2014, which is a divisional application of U.S. patent application Ser. No. 13/436,698, filed Mar. 30, 2012, which claims the benefit of U.S. provisional patent application No. 61/470,982, filed Apr. 1, 2011, the entire disclosures each of which are incorporated herein by reference.

TECHNICAL FIELD

A blister package for a pharmaceutical injection molded cartridge or capsule is disclosed.

BACKGROUND

Blister packaging systems may be used for protecting drug products in the pharmaceutical industry such as capsules, tablets, powders and liquids. Generally, blister packs consist of a rigid blistered base sheet having cavities or open blisters and a cover sheet or lid. Each blister in a pack normally contains the drug product in the form of a powder, capsule or tablet.

A drug delivery system for inhalation can include a cartridge for the delivery of a dry powder formulation to the pulmonary tract and lungs for the treatment of disease. Drug formulations contained in the cartridge may be used with a dry powder inhalation system, which delivers the drug content in a safe and consistent manner. Drug formulations used for pulmonary inhalation with a cartridge delivery system, however, may be sensitive to degradation, for example, by exposure to moisture. Thus, a cartridge containing the powder formulation may benefit from an improved packaging design to protect the cartridge and formulation from physical damage and environmental factors.

SUMMARY

Described herein are blister packages for protecting cartridges containing pharmaceutical formulations for use with an inhaler. In one example, cartridges used with a dry powder inhalation system are described in U.S. Pat. No. D613849 and U.S. patent application Ser. No. 12/484,137 (US 2009/0308392). Blister packages can be designed to contain, protect, dispense and/or improve the stability of a pharmaceutical formulation. In one embodiment, formulations can be designed for pulmonary delivery for the treatment of diseases, including, systemic and endocrine diseases such as diabetes. The blister packages can provide structural rigidity that resists curling of the material used and can also create a barrier to environmental factors such as moisture, light and/or dust; can facilitate dispensation of a dose of medicament to be administered to a patient. In one embodiment, the blister package can provide a high moisture barrier to protect a cartridge comprising a drug formulation during shipping, handling and/or storage of drug products prior to use.

In one embodiment, blister packages comprise a plurality of blisters which are uniform pocket-like wells, cup-like unit structures and/or cavities arranged in rows or arrays; wherein each unit of the blister package is configured to match correspondingly to the structure of a pharmaceutical cartridge or capsule containing a pharmaceutical formulation. In one embodiment, each blister well can house a corresponding cartridge. In another embodiment, the blister packages can comprise one or more irregularly shaped cavities or blister wells, wherein each cavity or blister well comprises a top, a bottom portion, an outer surface, an interior surface and a void. The bottom portion can comprise an outer surface having a substantially round end or dome, and a substantially flat end, or shelf extending from the dome area. In one embodiment, the substantially flat end can have an indentation or recess which forms a shelf or cartridge retaining feature in the interior surface, and the void area can be configured to house a cartridge comprising a cup-like container. In other embodiments, the blister packages can comprise a plurality of single unit blister wells which are separated from one another by a spacer or segment of unprocessed base material which is contiguous with an adjacent blister well. In this embodiment, the blister package can contain perforations or scored lines surrounding each blister unit to separate the blister unit to facilitate dispensation.

In one embodiment, the blister packages comprise one or more blister wells per row and one or more rows per blister package. In embodiments comprising two or more blister wells in a row of blisters, each blister well can be contiguous with another, and the internal volume or void of each blister well can be in communication with all blister wells. Alternatively, in some embodiments having more than one blister well that are contiguous with one another, each blister well can be separated so that the volume and/or void of each well may not be in communication with an adjacent blister well, any or all other blister wells. In one embodiment, the blister packs can comprise one or more rows of blister wells, wherein each row of blisters can be separated by perforation lines or scored along rows of blister wells or along lines surrounding each unit of the blister package.

One embodiment comprises a blister comprised of a base structure or material having formed cavities comprised of a thermoformable base laminate and a lid material, including a soft tempered aluminum foil with heat activated sealant. The base material and/or structure can comprise one or more layer of a thermoformable plastic, including, a polyvinyl chloride, a polyester, and/or a fluoropolymer, for example, a polychlorotrifluoroethylene (PCTFE) such as ACLAR® (Honeywell International Inc., NJ). In some aspects of the embodiments disclosed herein, the blister packages can comprise a base material comprising a laminated composite. In one embodiment, the laminate composite can comprise at least three layers selected from polyvinyl chloride and a fluoropolymer, such as an ACLAR layer and/or a material having similar thermoformable characteristics. In one embodiment, the laminated composite can be comprised of a three layer film structure comprising a first layer of polyvinyl chloride, or polyethylene pterephthalate (PET), a second layer of polyvinyl chloride, or PET, and a layer of a fluoropolymer including ACLAR, wherein the fluoropolymer layer comprises the middle layer of the laminated composite. In another embodiment, the blistered base sheet can comprise a fluoropolymer such as PCTFE adhesively bonded to PET.

In some embodiments, the laminated composite forming the base material can be made to have various thicknesses, and the thickness can depend on the degree of moisture barrier required for the formulation. In one embodiment, the thickness of the laminated composite of the blistered base sheet can range from about 230 µm to about 720 µm. In another embodiment the laminated composite blistered base sheet can be approximately 360 μm to about 610 μm in thickness. In this embodiment, blister packages made with the base laminates result in blisters with suitable rigidity and moisture barrier protection having a thickness greater than 100 μm.

In particular embodiments, blister packages may comprise one or more cavities and a cover or lid. Each of the cavities is configured to hold a cartridge which can be structured to be adapted to a dry powder inhaler and the cartridge can include a formulation for pulmonary delivery. The formulation can comprise an active ingredient, including but not limited to, a small molecule, protein, peptide, nucleic acid molecule or a combination thereof. In this and other embodiments, the cartridge can comprise a formulation for the treatment of for example, diabetes and the active ingredient in the formulation can be selected from peptides, including but not limited to, insulin, GLP-1, active fragments thereof, analogs thereof, or combinations thereof. In other embodiments, the active ingredient can be selected from any peptide or active agent that can be delivered by the pulmonary route, including, insulin, oxytocin, glucagon, parathyroid hormone, oxyntomodulin, peptide YY, glucagon like peptide 1, sumatriptan, peptidyl peptidase IV inhibitor, parathyroid hormone, neurotransmmiter agonist and antagonists, deoxyribonuclease I, active fragments thereof, analogs thereof, and combinations thereof.

Blister packages can be provided for single dosing, and/or multiple dosing, including, daily dosing of a pharmaceutical formulation, for two or more days, or a combination of multiple blisters can be provided for weekly or monthly supply as needed.

In still yet a further embodiment, blister packages can comprise a cartridge having a formulation for treating a disease comprising an inhalable dry powder composition comprising a diketopiperazine. In one embodiment, the diketopiperazine can have a formula 3,6-bis-(4-X-aminobutyl)-2,5-diketopiperazine, wherein X is selected from the group consisting of succinyl, glutaryl, maleyl, and fumaryl. In one embodiment, the dry powder composition can comprise a diketopiperazine salt; wherein the diketopiperazine salt can be an inorganic salt including, sodium, potassium, magnesium, lithium, cesium, and calcium. In another embodiment, the diketopiperazine can be an organic salt, including, triethylamine, butylamine, diethanolamine and triethanolamine. In still yet another embodiment, provided are dry powder compositions wherein the diketopiperazine is 3,6-bis-(4-fumaryl-aminobutyl)-2,5-diketopiperazine or a salt thereof, with or without a pharmaceutically acceptable carrier, or excipient. Blister packages can also comprise a cartridge with a formulation with pharmaceutically acceptable carriers and/or excipients including, but not limited to lactose, dextran, amino acids, and the like.

BRIEF DESCRIPTION OF THE DRAWINGS

FIG. 10 illustrates a top view of a blister pack as described herein.

FIG. 11A illustrates a back view of a piercing seal as described herein. FIG. 11B illustrates a pealable seal as described herein.

FIG. 12 is a graph of data obtained from experiments showing the typical Water Vapor Transmission Rate (WVTR) of the blister package embodiment disclosed herein.

FIG. 17 illustrates standard deviations for the graphs of FIGS. 14-16.

Embodiments of the present disclosure are exemplified only and are not limited to the drawings disclosed in FIGS. 1-17.

DETAILED DESCRIPTION

Described herein are blister packages configured to protect a cartridge or capsule containing a pharmaceutical formulation for pulmonary delivery. The cartridges or capsules can be used in conjunction with an inhaler.

Figure 1:
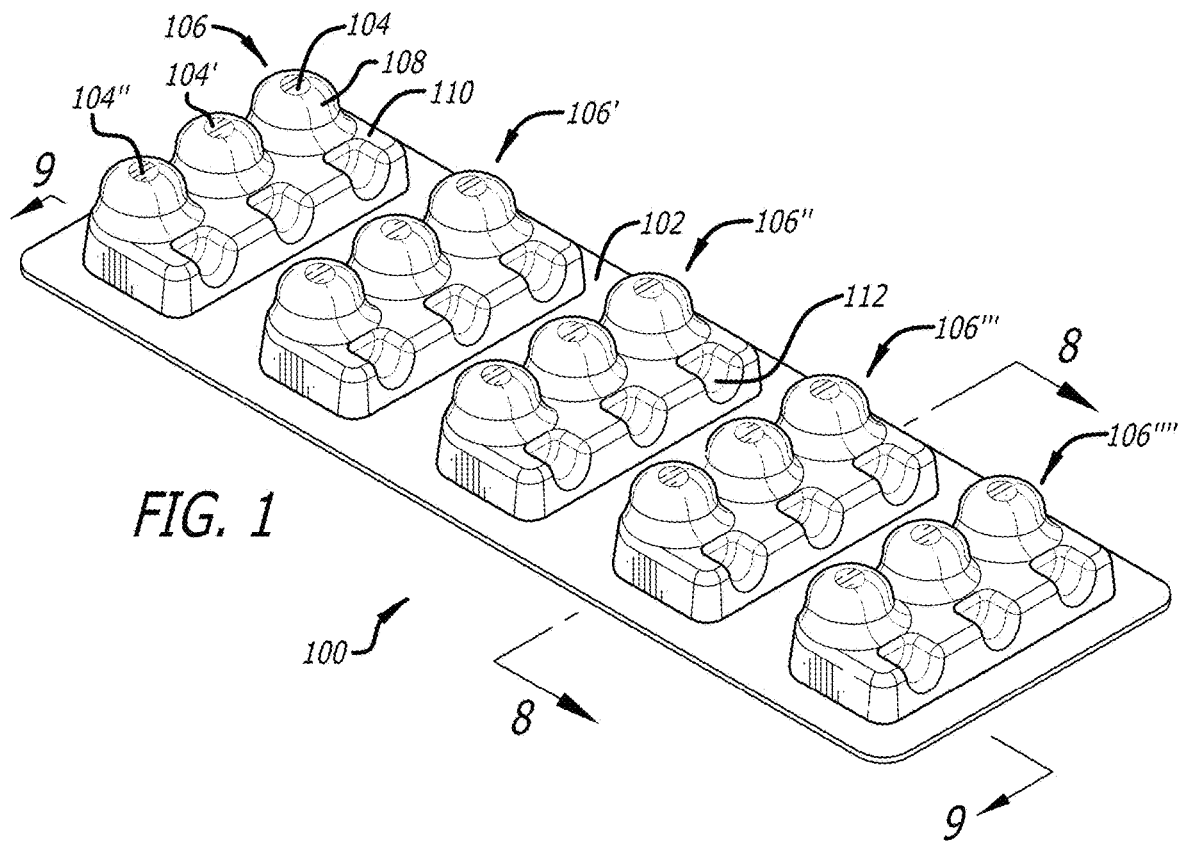
FIG. 1 is a perspective view of a blister packaging embodiment disclosed herein.

FIG. 1 illustrates an isometric view of an exemplary embodiment of blister package 100 described herein. Blister package 100 comprises a blister card or blistered base sheet 102 having a plurality of molded cavities 104, 104', 104", 104''', 104'''', etc. arranged in one or more rows 106, 106', 106", 106''', 106'''', etc. In one embodiment, three domes 108 can be present in each row 106. Cavity 104 can comprise a first substantially round end or dome 108 and a somewhat flat area structure or shelf 110 which protrudes from dome 108 and forms a cartridge lid retention feature 112 therein forming an indentation or depression in the cavity outer surface. Dome 108 may be configured to accommodate a unit dose cartridge container or cup, and shelf 110 may be configured to contain and hold a section of a cartridge lid or top assembly in a cartridge containment or pre-dosing configuration. A pharmaceutical cartridge which can be packaged within the present blister package can be one depicted, for example, in U.S. Pat. D613849 and US 2009/038390, the disclosures of which are hereby incorporated in their entirety for all they disclose regarding cartridges.

The cartridge lid retention feature or shelf can hold a lid of a cartridge in place, and/or prevent cartridges in multiple cartridge blisters from contacting adjacent cartridges. In one embodiment, a cartridge stored in a present blister unit which cartridge comprises a cartridge lid and a container in containment or pre-dosing configuration, the cartridge container is adapted to the dome of the blister unit and suspended by the lid adapted to the shelf of the blister. In this manner, the cartridge container is prevented from moving and maintained in containment configuration.

FIG. 1 also illustrates blister package 100 containing five rows 106 of each containing three cavities 104 each. This embodiment can be suitable for three times a days dosing for a patient. In some embodiments, a dose with every meal can be a prescribed inhalable dose of insulin or other medication for patients with a condition such as but not limited to diabetes. Alternate embodiments can be used depending on the disease to be treated.

Other embodiments can have one, two three, four, five, six, seven, eight, nine, ten, eleven, twelve, thirteen, fourteen, or fifteen cavities in each row. A blister package can further include one, two three, four, five, six, seven, eight, nine, ten, eleven, twelve, thirteen, fourteen, or fifteen rows.

Blister package 100 illustrated in FIG. 1 can be configured to nest with another blister package so that the blisters from opposing packages can intercalate between two rows 106 of the other package in reducing the size of the outer package during shipping. Blister package 100 can be married with another blister pack turned backward and upside down to reduce packaging size. Other means can be envisioned for reducing packaging size, bulk or the like.

In embodiments herein, the blisters can be configured to match the specific cartridge size to be packaged. The size of rows in a blister package also can vary depending on factors such as the number of blister wells per row and the size of the blisters. In one embodiment, each blister well or cavity 104 can be greater than about 1 cm in length; greater than 1 cm in height at dome 108, and greater than 1 cm in width. In one embodiment, the size of cavity 104 can be about 1.5 cm in width, approximately 2.5 cm in length and about 1.5 cm in height; wherein rows 106 within a blister package can be each about 6 cm in length and about 3.5 cm in width. In this and other embodiments, cavities 104 can be configured centrally within a blister row or segment of a blister package.

Figure 2:
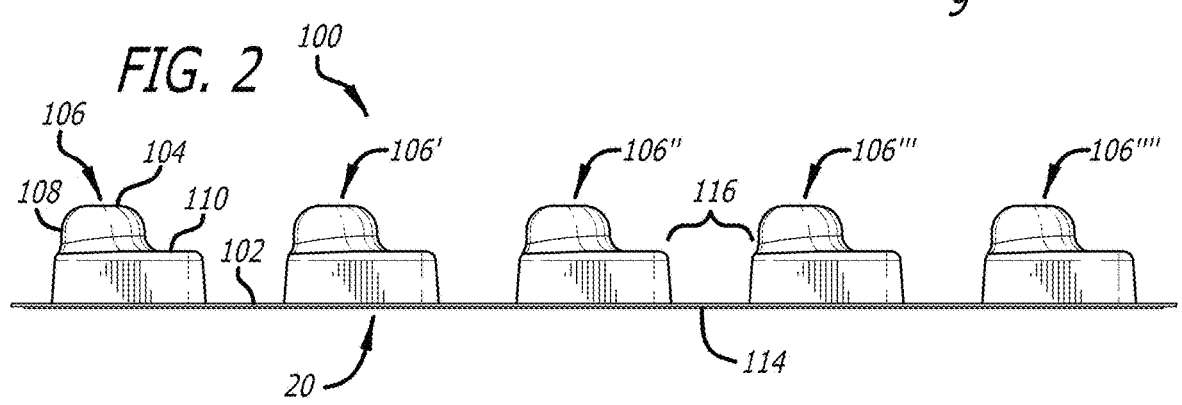
FIG. 2 is a first side view of the blister packaging in FIG. 1 depicting the uniform arrangement of the rows of blisters within the package.
Figure 3:
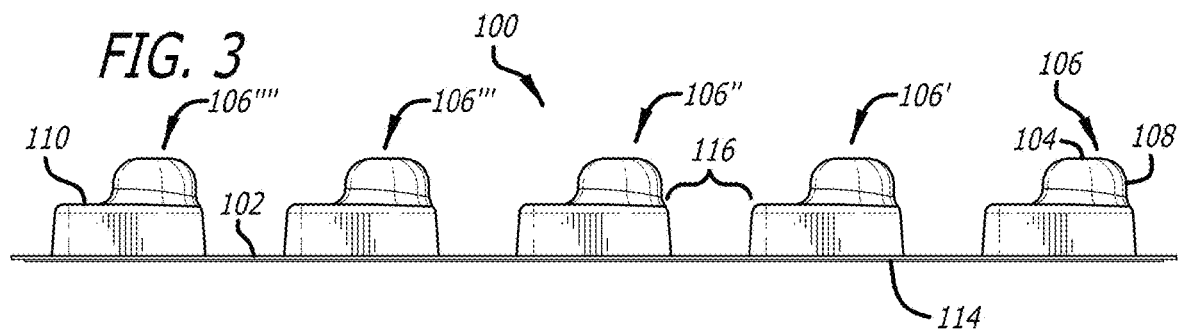
FIG. 3 is a second side view of the blister packaging embodiment in FIG. 1, showing the blister rows from the opposing side of FIG. 2.

FIGS. 2 and 3 each illustrate opposing side views of blister package 100 illustrated in FIG. 1. Depicted in FIGS. 2 and 3 is the uniform arrangement of rows 106 within blister package 100. FIGS. 2 and 3 also depict dome 108 and shelf 110 shapes having what can be an overall substantially elongated shape. Cavities 104 can have a flat end or shelf extending laterally from a dome structure. FIGS. 2 and 3 also illustrate blistered base sheet 102 forming blister wells or cavities 104 and lid 114 is shown sealing the cavities 104.

Figure 4:
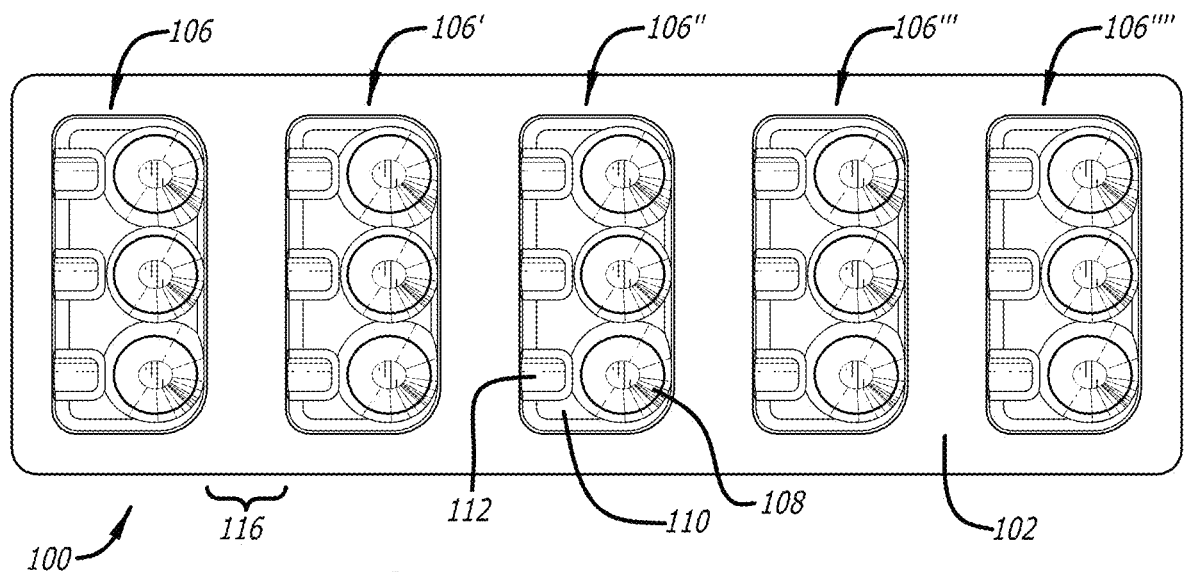
FIG. 4 is a bottom view of the blister packaging embodiment in FIG. 1, showing the blisters organization within the package.

FIG. 4 is a bottom view of blister package 100 illustrated in FIG. 1, showing cavities 104 organized within blister package 100. In this embodiment, blister package 100 comprises rows 106 configured having space 116 between rows 106. In one embodiment, domes 108 from a first blister package can fit in space 116 between rows 106 of a second blister package and shelves 110 of the first blister package can abut shelves 110 of the second blister package.

Figure 5:
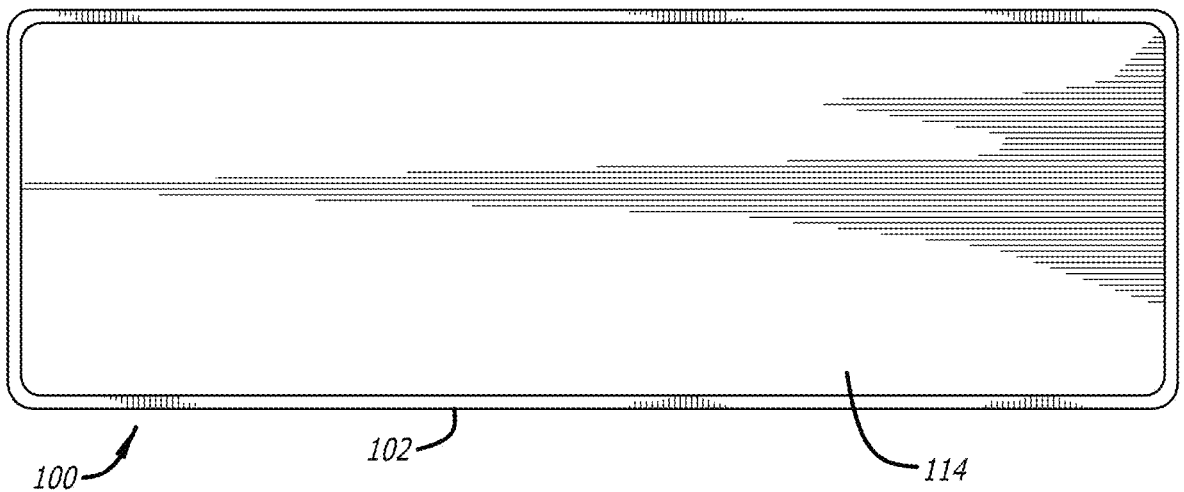
FIG. 5 is a top of the blister packaging embodiment in FIG. 1, showing the lid.

FIG. 5 is a top view of blister package 100 illustrated in FIG. 1, illustrating lid 114 sealing of blister package 100. Lid 114 can be bonded or sealed so that lid 114 adheres to flat surfaces of blistered base sheet 102. One portion of blistered base sheet where lid 144 can adhere is space 116 between cavities 104 and over each cavity opening. This adherence of lid 114 to blistered base sheet 102 can close blister package 100 and encapsulate one or more cartridges within cavities 104. In one embodiment, lid 114 can be a single sheet that covers the entire blistered base sheet 102 and bonds with the blistered base sheet in the areas surrounding cavities 104.

In some embodiments, lid 114 can be adhered to the back portion of blistered base sheet 102 flush with all of underside of blistered base sheet 102. In other embodiments lid 114 can adhere to the underside of blistered base sheet 102, but be smaller than blistered base sheet 102. In still other embodiments, lid 114 can be larger than the underside of blistered base sheet 102 and wrapped around the edges of blistered base sheet 102.

Figure 6:
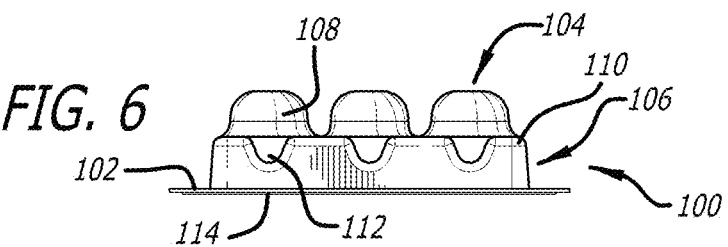
FIG. 6 is a front view of the blister packaging embodiment in FIG. 1, showing a row of three blisters and their configuration depicting a dome area and their side indentations or cartridge retention features.
Figure 7:
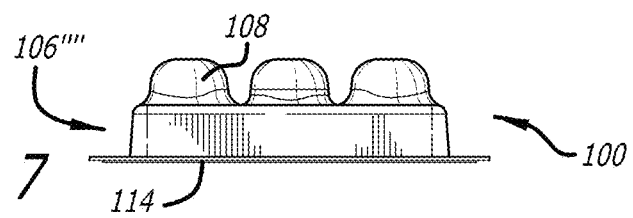
FIG. 7 is a back view of the blister packaging embodiment in FIG. 1.

FIGS. 6 and 7 are, respectively, front and back views of blister package 100 illustrated in FIG. 1, illustrating blister package 100 comprising row 106 including three combined cavities 104. Each section of cavity 104 can include dome 108 and its lateral shelf 110 with indentations or cartridge retention features 112; wherein the rows of blisters are sealed with lid 114.

Figure 8:
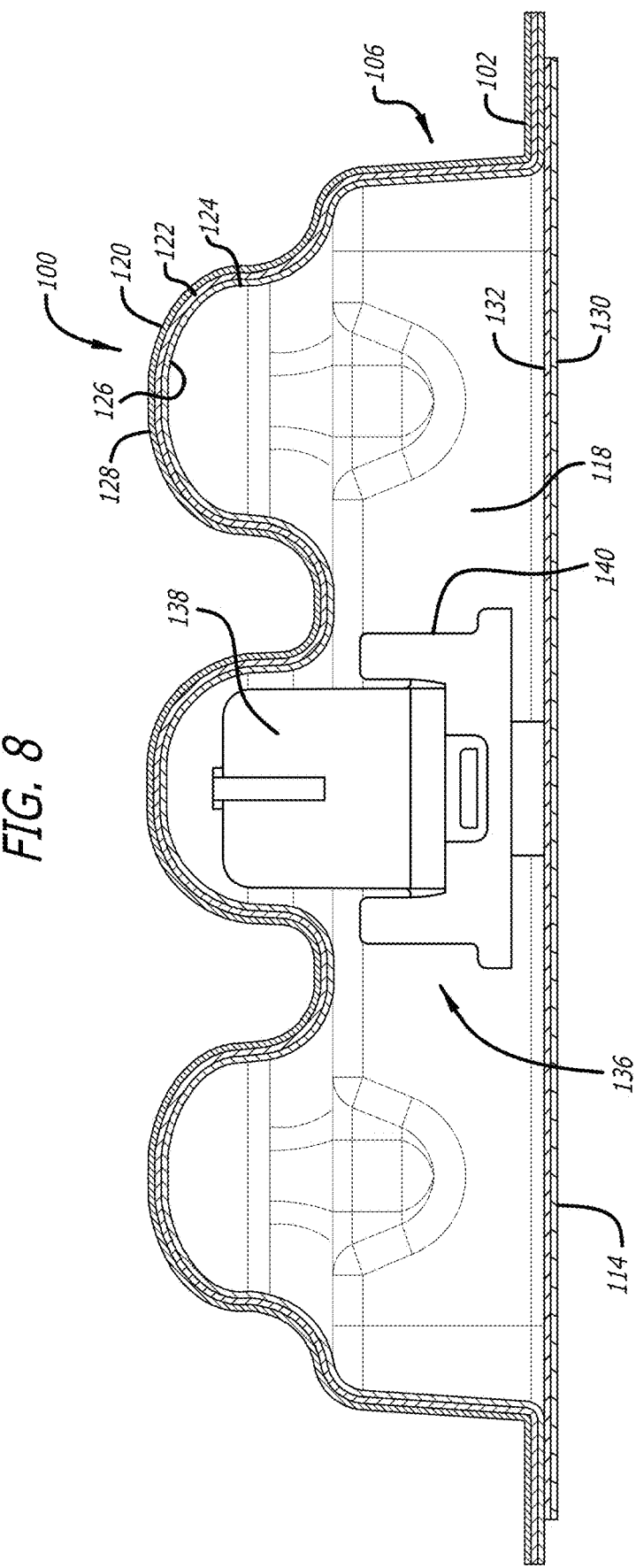
FIG. 8 is a cross-section of a row of blisters through plane 8 to 8 as shown in FIG. 1.

FIG. 8 illustrates a cross-section through a row of cavities as depicted in FIG. 1 through plane 8 to 8. FIG. 8 illustrates an interior of three interconnected cavities and their relationship with one another within a row. This figure illustrates internal volume 118 or void of row 106. FIG. 8 also illustrates a view of an embodiment of blistered base sheet 102 showing component layers. In this embodiment, blistered base sheet 102 comprises a three layer film laminate including first layer 120, second layer 122 and third layer 124. Each of the three layers can be adhesively bonded to each other. In other embodiments, more or less than three layers can be used. For example, one, two, three, four, five, six, seven, eight, nine, or ten layers can be used. In one embodiment, the number of layers used can be the number or thickness needed to substantially prevent water infiltration into a sealed packaging (blistered base sheet and lid).

In one embodiment, blistered base sheet 102 can be manufactured using thermoformable plastics. In certain embodiments, blistered base sheet 102 can be a thermoformable laminate formed from films comprising one or more than one layer of a thermoformable plastic, including, polyester, polyvinyl chloride, and/or a fluoropolymer, such as ACLAR®. In other embodiments, blister package 100 comprises a laminated composite comprising at least three layers selected from a polyvinyl chloride layer, PET and a fluropolymer layer, wherein at least one layer is a fluoropolymer. In one aspect of this embodiment, blistered base sheet 102 can be formed of a fluoropolymer layer and two polyvinyl chloride layers. In one embodiment, first layer 120 can be polyvinyl chloride, second layer 122 can be a fluropolymer layer, and third layer 124 can be polyvinyl chloride. In such an embodiment, first layer 120 and third layer 124, both of which are polyvinyl chloride layers, form inner surface 126 and outer surface 128 of each cavity 104.

Other polymers that can be used alone or in combination with the above to form a blistered base sheet 102 can include poly(L-lactic acid), polycaprolactone, poly(lactide-co-glycolide), poly(ethylene-vinyl acetate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly (ether-esters) (e.g., PEO/PLA), polyurethanes, silicones, polyesters, polyolefins, polyisobutylene and ethylene-alphaolefin copolymers, acrylic polymers and copolymers, ethylene-co-vinylacetate, polybutylmethacrylate, vinyl halide polymers and copolymers (e.g., polyvinyl chloride), polyvinyl ethers (e.g., polyvinyl methyl ether), polyvinylidene halides (e.g., polyvinylidene fluoride and polyvinylidene chloride), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), polycarbonates, polyoxymethylenes, polyimides, polyethers, polyurethanes, rayon, cellophane, and carboxymethyl cellulose.

Blistered base sheet 102 can be transparent, partially transparent or opaque. Partially transparent includes materials that allow about 5%, about 10%, about 15%, about 20%, about 30%, about 40%, about 50%, about 60%, about 70%, about 80%, about 90% of light through. Opaque materials can allow substantially no light through and can be useful to house medicaments sensitive to light.

The thickness of the laminate material prior to forming the blistered base sheet can be about 10 µm, about 25 µm, about 50 µm, about 75 µm, about 100 µm, about 125 µm, about 150 µm, about 175 µm, about 200 µm, about 225 µm, about 250 µm, about 275 µm, about 300 µm, about 325 µm, about 350 µm, about 375 µm, about 400 µm, about 425 µm, about 450 µm, about 475 µm, about 500 µm, about 525 µm, about 550 µm, about 575 µm, about 600 µm, about 625 µm, about 650 µm, about 675 µm, about 700 µm, about 725 µm, about 750 µm, about 775 µm, about 800 µm, about 825 µm, about 850 µm, about 875 µm, about 900 µm, about 925 µm, about 950 µm, about 975 µm, about 1000 µm, about 1025 µm, about 1050 µm, about 1075 µm, about 1100 µm, about 1125 µm, about 1150 µm, about 1175 µm, or about 1200 µm thick, or any thickness in a range bound by or between any of these values. In some embodiments a overall thickness can range from about 100 µm to about 750 µm.

Each layer in the laminate material can have a thickness and the total thickness of all the layers can represent the total thickness of the laminate material. Each layer can have a thickness of about 10 µm, about 25 µm, about 50 µm, about 75 µm, about 100 µm, about 125 µm, about 150 µm, about 175 µm, about 200 µm, about 225 µm, about 250 µm, about 275 µm, about 300 µm, about 325 µm, about 350 µm, about 375 µm, about 400 µm, about 425 µm, about 450 µm, about 475 µm, about 500 µm, about 525 µm, about 550 µm, about 575 µm, about 600 µm, about 625 µm, about 650 µm, about 675 µm, about 700 µm, about 725 µm, about 750 µm, about 775 µm, about 800 µm, about 825 µm, about 850 µm, about 875 µm, about 900 µm, about 925 µm, about 950 µm, about 975 µm, about 1000 µm, about 1025 µm, about 1050 µm, about 1075 µm, about 1100 µm, about 1125 µm, about 1150 µm, about 1175 µm or any thickness in a range bound by or between any of these values. In embodiments wherein ALCAR is used, that layers thickness can range from about 230 µm to about 720 µm in thickness.

The structure of the blistered base sheet 102 can provide a required vapor and/or moisture barrier which can improve the stability of a pharmaceutical formulation, while also providing structural rigidity that resists curling of the laminate. As discussed above, the blistered base sheet and lit sealed combination can substantially prevent water infiltration into a sealed packaging. Curling of the laminate material is a trait that prior art blisters possess when manufactured of the size and length required to contain an inhaler cartridge of the sizes disclosed herein.

Blister package 100 in FIG. 8 can further comprise top or lid 114 which can be formed of a film or sheet including one or more layers of a material. Materials suitable in manufacturing lid 114 can include but are not limited to a foil material such as aluminum, copper and/or a polymer or co-polymer. Polymers can include polyesters such as polyethylene terephthalate (PET) and/or glycol-modified polyethylene terephtalate (PETG). Other Polymers that can be used include poly(L-lactic acid), polycaprolactone, poly(lactide-co-glycolide), poly(ethylene-vinyl acetate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g., PEO/PLA), polyurethanes, silicones, polyesters, polyolefins, polyisobutylene and ethylene-alphaolefin copolymers, acrylic polymers and copolymers, ethylene-co-vinylacetate, polybutylmethacrylate, vinyl halide polymers and copolymers (e.g., polyvinyl chloride), polyvinyl ethers (e.g., polyvinyl methyl ether), polyvinylidene halides (e.g., polyvinylidene fluoride and polyvinylidene chloride), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), polycarbonates, polyoxymethylenes, polyim ides, polyethers, polyurethanes, rayon, cellophane, and carboxymethyl cellulose.

Lid 114 in FIG. 8 comprises a two-layer film. However, in other embodiments, lid 114 can include one, two, three, four, five, six, seven, eight, nine, or ten layers can be used. In one embodiment, the number of layers used can be the number or overall thickness needed to substantially prevent water infiltration into a sealed packaging. Lid 114 can comprise an overall thickness from about 5 µm to about 100 µm, about 10 µm to about 75 µm, or about 20 µm to about 50 µm. Each material layer used to form lid 114 can have a thickness of about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, or about 95 µm, or any thickness in a range bound by or between any of these values. In one embodiment, lid 114 can be between about 30 µm and about 150 µm thick. In another embodiment, lid 114 can be about 30 µm thick and manufactured from an outer layer 130 of soft tempered aluminum foil, a primer and over-lacquer layer and an inner layer 132 of a heat sealed polymeric coating. The soft tempered foil can resist puncture and tearing and can provide a level of durability to the package.

Figure 9:
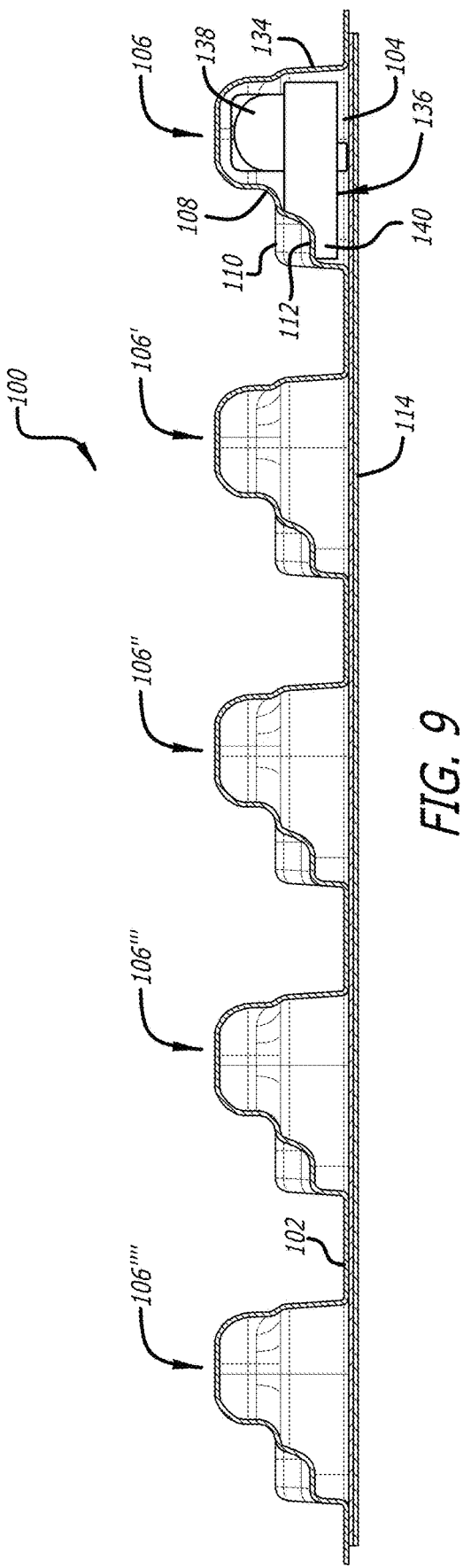
FIG. 9 is a longitudinal section of the blister package through plane 9 to 9 traversing the midpoint of blister wells.

FIG. 9 illustrates a longitudinal cross-section of blister package 100 comprising five rows of blisters and traversing dome 108 in each of the rows 106. In this figure, only a single layer 134 of polymer material is used to form blistered base sheet 102, but as described above, more layers can be used. Lid 114 includes both outer layer 130 and inner layer 132. However, as described above, more or fewer layers can be used to form lid 114.

In one embodiment as illustrated in FIG. 9, cartridge 136 is shaped to fit within a cavity 104. Cup portion 138 of cartridge 136, wherein a dry powder medicament can be housed, can fit into dome 108 and top portion 140 of cartridge 136 can rest on the combination of shelf 110 and cartridge lid retention feature 112. However, any cartridge can fit within a blister package as described herein. Blistered base sheets can be customized to fit additional and/or different cartridges.

FIG. 10 illustrates an embodiment wherein a cartridge can be housed in an independent cavity 142. Here, blistered base sheet 144 can meet with lid 114 between each cavity 142, 142' 142" in a row 106. As such, a channel 146 can be formed between each adjacent cavity 142 in which blistered base sheet and lid material can be bonded to each other. As above, each cavity here can still include dome 108, shelf 110 and cartridge lid retention feature 112.

Additionally, in FIG. 10, perforations 148 in the blistered base sheet 144 can be included in order to give a patient the ability to tear away a row of blister pack 100 to reduce bulk to transport. As in some embodiments, three doses a day can be prescribed, simply tearing a row off of a blister pack can be a useful feature for a days worth of medicine. In other embodiments, perforations can be included allowing each cavity of blistered base sheet 144 to be individually removed.

The bond between lid 114 and blistered base sheet 144 (see FIG. 9) can vary depending on the particular need. In one embodiment, the bond between lid 114 and blistered base sheet 144 can be permanent so that the foil must be breached to access the contents of a cavity. As illustrated in FIG. 11A, lid 114 can be punctured 150 allowing individual cartridges to be removed from a particular cavity 104 in blistered base sheet 144. In other embodiments including blistered base sheet 102 (FIG. 4), lid 114 can be punctured allowing multiple, for example, three cartridges to be revealed.

In another embodiment, the bond between lid 114 and blistered base sheet 102 can be semi-permanent so that the foil can be pealed to access the contents of a cavity. As illustrated in FIG. 11B, lid 114 can be pealed 152 allowing individual cartridges to be removed from a particular cavity 104 in blistered base sheet 144. In other embodiments including blistered base sheet 102, (FIG. 4) lid 114 can be pealed allowing multiple, for example, three cartridges to be revealed. In some embodiments, peal perforation 154 can be included so that after pealing beyond a row 106, the lid can be torn away at peal perforation 154 and discarded.

In another embodiment disclosed herein, are methods of manufacturing blister packages as described herein in an automated in-line fashion on a commercially available blister thermoforming machine. The methods can comprise providing a base material or sheet and a lid film; loading the base material and lid film onto the machine in roll form and processing the base material and lid film in the machine. The process can be performed according to the manufacture's recommendations. In one embodiment, the base material is drawn into a forming station where it can be formed using heat at a temperature ranging from about 120° C. to about 150° C., or from about 120° C. to about 135° C.; and/or air pressure and mechanical plugs configured to form the blister cavities or wells at a predetermined cycle, for example, between 10 and 30 cycles per minute, or from about 12 to about 25 cycles per minute. In one embodiment the air pressure can be set for about 4 to about 7 bars, or from about 5 to about 6 bars. The heat, air pressure and mechanical plugs to be used depend on the size of the blister well size to be made and the base material used. The cartridge product can be automatically loaded into the blister cavities, then, the lid stock is pulled over it. Together the formed and filled base material and the lid are pulled into the sealing station where heated tools cause the activation of the sealant layer on the lid, creating a sealed blister package. After sealing, the web of formed and filled blisters is pulled into a perforating station and then finally a die cutting station that creates the final blister package.

In one embodiment, a blister package can be designed to contain 15 drug filled cartridges. In such an embodiment, the drug filled cartridges can be situated in five rows of three. In another embodiment, a blister package can be designed to contain 21 drug filled cartridges. In such an embodiment, the drug filled cartridges can be situated in seven rows of three. Cartridges that can be used with the blister packages can be for pharmaceutical formulations intended for pulmonary delivery. In some embodiments, the pharmaceutical formulations that can be contained in the cartridges are in particular for delivering biologics, including, peptides and proteins and other drugs that are sensitive to degradation. In some embodiments, the cartridge in the blister contains a formulation comprising a diketopiperazine such as those disclosed in U.S. Pat. Nos. 7,794,754; 7,799,344; 7,803,404; 6,444,226; 6,555,127; 6,440,463; 6,428,771; 6,071,497; 5,352,461 and 5,503,852; and patent application Ser. No. 12/813,839 (US 2010/317574) and WO 2010/144789, which disclosures are incorporated herewith in their entirety for all they contain regarding diketopiperazines and drug formulations. An exemplary diketopiperazine, includes fumaryl diketopiperazine (bis-3,6-(N-fumaryl-4-aminobutyl)-2,5-diketo-diketopiperazine; FDKP). An FDKP is one diketopiperazine used for pulmonary applications and has a formula:

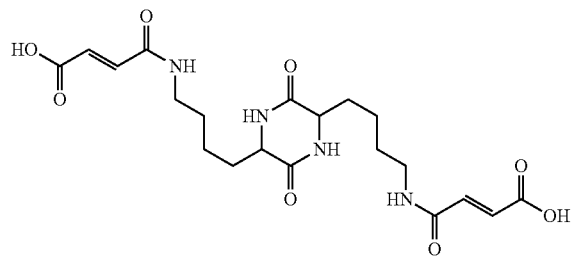 [SMILES: O=C(O)/C=C/C(=O)NCCCCC1NC(=O)C(CCCCNC(=O)/C=C/C(=O)O)NC1=O]

FDKP provides a beneficial microparticle matrix because it has low solubility in acid but is readily soluble at neutral or basic pH. These properties allow FDKP to crystallize and the crystals to self-assemble into form microparticles under acidic conditions and are suitable for pulmonary delivery having a diameter of between about 0.5 and about 10 microns can reach the lungs, successfully passing most of the natural barriers. Cartridges containing formulations for pulmonary delivery comprising salts of diketopiperazines such as those disclose in U.S. Pat. No. 7,820,676 and other formulations for use the cartridges can also be package into the present blister package.

In one embodiment, a method for assembling the blister package containing a cartridge in each blister is disclosed. In one embodiment, the cartridge can be a two part cartridge (as described above) comprising a container or cup and a lid or top as depicted and described in U.S. Pat. No. D613849 and U.S. patent application Ser. No. 12/484,137 (US 2009/0308392), respectively. The cartridge can further comprise a containment or pre-dosing configuration and a dosing configuration. In the embodiments herewith, the method comprises providing cartridges consisting of two injection molded parts, each cartridge comprising a lid and a cup; filling the cup with a drug formulation; placing a cartridge lid over the cup, and locking the top to the cup into a transport or containment configuration so that the drug powder is sealed in the cup. In this and other embodiments, the blister package is designed to transport the cartridges while preventing the premature movement of the cartridge cup into the dosing configuration.

Accordingly, blister packages can be designed to prevent movement of the cartridge within the blister cavity which is achieved by forming a series of formed-in features that cradles each cartridge within the blister well and also prevents them from touching each other. In this and other embodiments, blister package 100 can be configured so that each blister or cavity 104 comprises shelf area 110 wherein the lid of the cartridge in a containment configuration can rest on the shelf area 110, which in turn allows the cup to be suspended down into dome 108 or circular void of the blister, protecting a drug product from mechanical shock. In this embodiment, the cartridge cup in the blister can be surrounded on all sides by the dome-like feature, and it may not be possible for the cup to slide into the dosing position while the cartridge is in the blister package.

In one embodiment, blister package 100 can also be designed and configured to nest with the blisters from another blister pack so as to reduce the size of the distributed package during shipping and storage of the product. In one embodiment, the method comprises turning or flipping one blister package 100 over so that a pair of blister packages can face each other cavity to cavity then bringing them together so that the undersides of the blister shelf areas 110 on the opposing blisters make contact. This arrangement may allow for a pair of blister packages to be over-wrapped together in a smaller footprint to what it would be if the blister packages were simply stacked. In one embodiment, a pharmaceutical pack can comprise one or more blister packages as described herein; wherein the blister package is enclosed in a foil over-wrapped and the foil over-wrap comprises a soft-tempered aluminum material.

In an exemplary embodiment, blister package 100 can be used for three times a day use for a five-day supply. Such a blister package consists of five thermoformed cavities 104 designed to hold three drug filled cartridges 136 each per row 106. Each cavity 104 of three cartridges can have an area extending about five millimeters which forms a seal on all four sides and the seal tooling can be knurled to further increase the total seal area.

A perforation, as described above, can be provided between each blister unit, including a section, or row 106 so that each section can be separated from the adjoining section. Individual cavities 104 of, for example, one, two, three or more cartridges can be discretely carried in the pocket or purse. In this manner, an end user can carry only as much drug product as may be needed for any particular dosing event. In one embodiment, to remove a cartridge, the user presses on the blister dome with a thumb or finger, causing the cartridge to break through the soft foil lid. This method of blister removal is commonly called push through. If done carefully, a single cartridge can be removed from a common cavity of, for example, three having a contiguous volume without displacing the other two. Alternative configurations can be made depending on the drug to be delivered and the number of doses a patient would need for a period of time.

In some embodiments, processed blister packages can have reproducibly thick laminate thicknesses through the cavities. In some embodiments, the standard deviation can be between about 0.004 mm and about 0.023 mm.

In other embodiments, once sealed, a blister package described herein can resist substantially all water ingress for a period of about 1 week, about 1 month, about 6 months, about 1 year, about 2 years, about 3 years, about 4 years or about 5 years. For example, less than about 0.05 g, less than about 0.02 g, less than about 0.01 g, less than about 0.001 g, or less than about 0.0001 g of water may make its way into a sealed blister packaging or to a medicament. In another embodiment the blister packages described herein can resist water transmission when stored at a refrigerated temperature, for example, at 4° C.

In some embodiments, water vapor transmission rate can be less than about 0.005 g water per package per day. In other embodiments, the water transmission rate can be less than about 0.003 g, 0.002 g, 0.001 g, 0.0005 g, 0.00005 g, 0.00001 g, or 0.000005 g water per package per day. In one embodiment, the water transmission is less than about $4.0 \times 10^{-5}$ g water per package per day.

Water vapor transmission rate can also be affected by storage temperature. Blister packages described herein can resist water transmission when stored at temperatures between about 10° C. and about 35° C., about 15° C. and about 30° C., about 20° C. and about 25° C. In one embodiment, the blister packages described herein can resist water transmission when stored at room temperature.

In one embodiment, not only are blister packages sealed but also a cartridge(s) within the blister packaging can also have a sealed container including a medicament. In some embodiments, the medicament is a dry powder as described herein. In some embodiments, this dry powder can resist substantially all water ingress for a period of about 1 week, about 1 month, about 6 months, about 1 year, about 2 years, about 3 years, about 4 years about 5 years or about 10 years.

Example 1

Manufacture of Blister Package Assembly

Rolls of base material or sheet and lid film are provided in connection with a commercial thermoformer (Pharmworks TF-2X). The base material consists of a fluoropolymer layer in between two polyvinyl chloride layers manufactured by Klockner Pentaplast of America. The base material is drawn into a forming station at a speed of from about 12 to 25 cycles per minute (cpm), where it is formed using a combination of heat, air pressure and mechanical plugs specifically designed in the dimensions required to make the blisters as defined in the FIGs. In this example, temperature for softening the plastic to form the blister wells can range from about 130° C. to about 150° C. The cartridges containing the pharmaceutical formulation are automatically loaded into the blister cavities, then the lid stock consisting of a soft tempered aluminum foil (Alcan) is pulled over this assembly. Together the formed and filled base material and the lidding are pulled into the sealing station where heated tools at temperatures ranging from about 150° C. to about 170° C. and pressure cause the activation of the sealant layer on the lidding, creating a sealed blister. After sealing, the web of formed and filled blisters is pulled into a perforating station and then finally a die cutting station that creates the final blister package.

Example 2

Water Vapor Transmission Rates of Blister Packs

Blister packages manufactured in Example 1 were tested for rate of water vapor transmission. Sealed blister packages comprising a tri-laminar blistered base sheet comprised of an outer and inner layer of polyvinyl chloride and a middle layer of ACLAR and a soft temper foil lid were compared to blister packages made from a blistered base sheet consisting of a single layer of PET similar in gauge thickness to the tri-laminar blistered base sheet and having a soft temper foil lid. Each blister package was injected with 3 ml of water (1 ml in each of three blisters) using a syringe with a 29 gauge (0.33 mm×13 mm) needle through the base of the blister package. After injecting the water, the hole in the base material was plugged with quick curing epoxy adhesive. Water vapor traversing the package was analyzed over a period of time by passing a stream of clean dry nitrogen gas over the package in a sealed glass container and measuring the quantity of moisture picked up by the nitrogen gas. Measurement of water vapor traversing the package and released into the sealed jar was analyzed at the onset of the experiment and for a period of time thereafter in a Mocon Permatran apparatus.

FIG. 12 is a graph depicting data from the experiment illustrating the typical Water Vapor Transmission Rate (WVTR) of the blister package wherein grams of moisture per day are shown on the vertical axis, and time points tested are shown on the horizontal axis. Curve A (tri-laminar blistered base sheet comprising ACLAR) and curve B (PET blistered base sheet) illustrates the results of the experiments. The data illustrate that after a short period of time where the test instrument purges itself of air, the WVTR quickly stabilizes to a level where the water vapor transmission rate is stable and almost non-detectable after six days of testing. This demonstrates that the package integrity is acceptable over time. Comparative data from the blister made using conventional PET laminates as shown in FIG. 12, curve B show that this material is not as effective in preventing moisture transmission through the package. It can also be noted in FIG. 12 that the initial peak associated with curve A is water vapor present in the jar (atmospheric) at onset of the experiment, which requires about 12 hours to evacuate.

Example 3

Blistered Base Sheet Cavity Uniformity

In these experiments, three different blistered base sheet laminates were manufactured similarly as described in Example 1, using a temperature setting ranging from 120 to 125° C. for making the blistered base sheets and a sealing temperature setting between 155 and 165° C. at 12-25 cycles per minute and at an air pressure of about 6 bars. Thicknesses of the cavities on the blistered base sheet were measured at various locations as indicated in FIG. 13 to determine integrity and uniformity of blisters or cavities.

Figure 13:
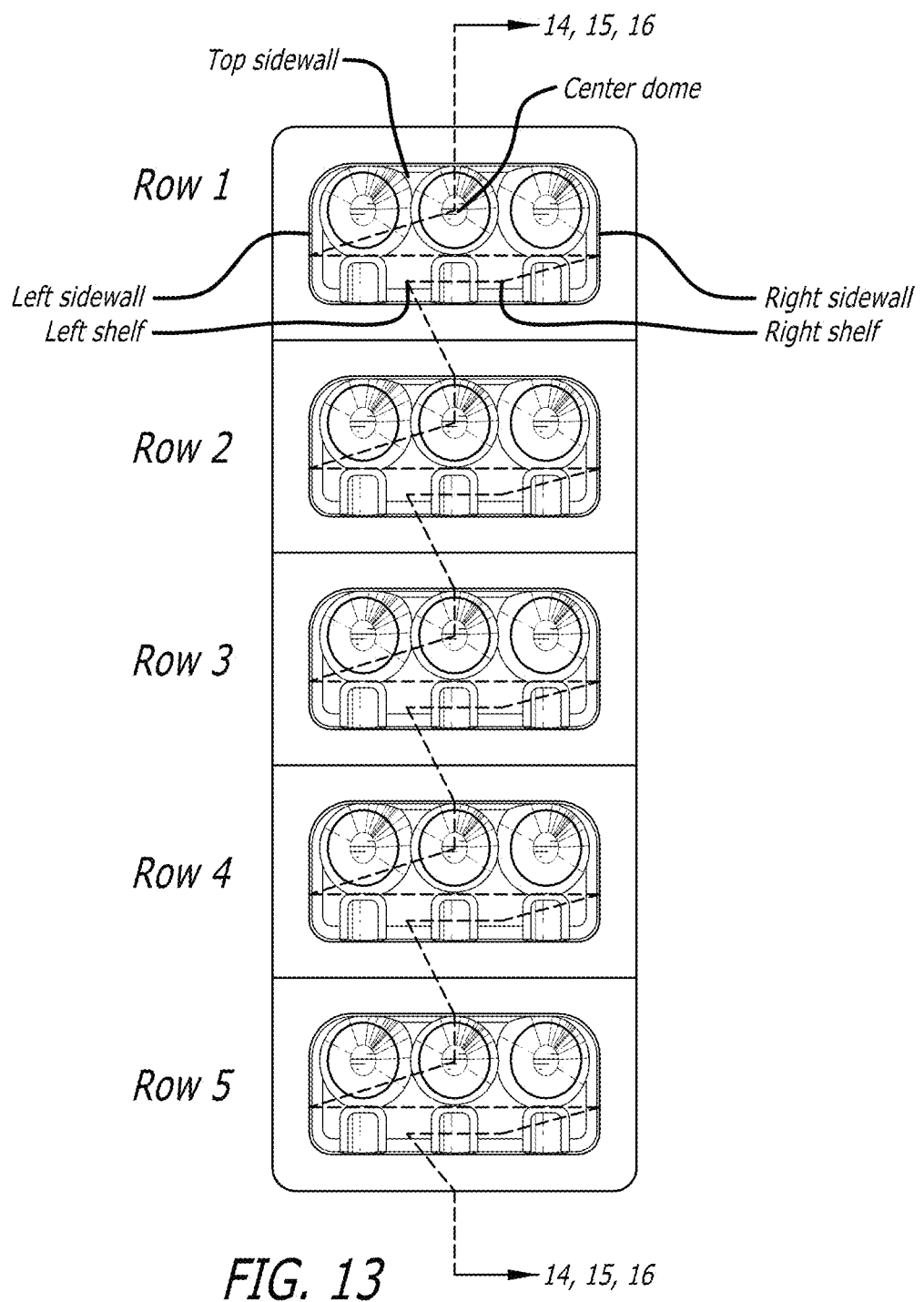
FIG. 13 illustrates a top view of a blister package as described herein.
Figure 14:
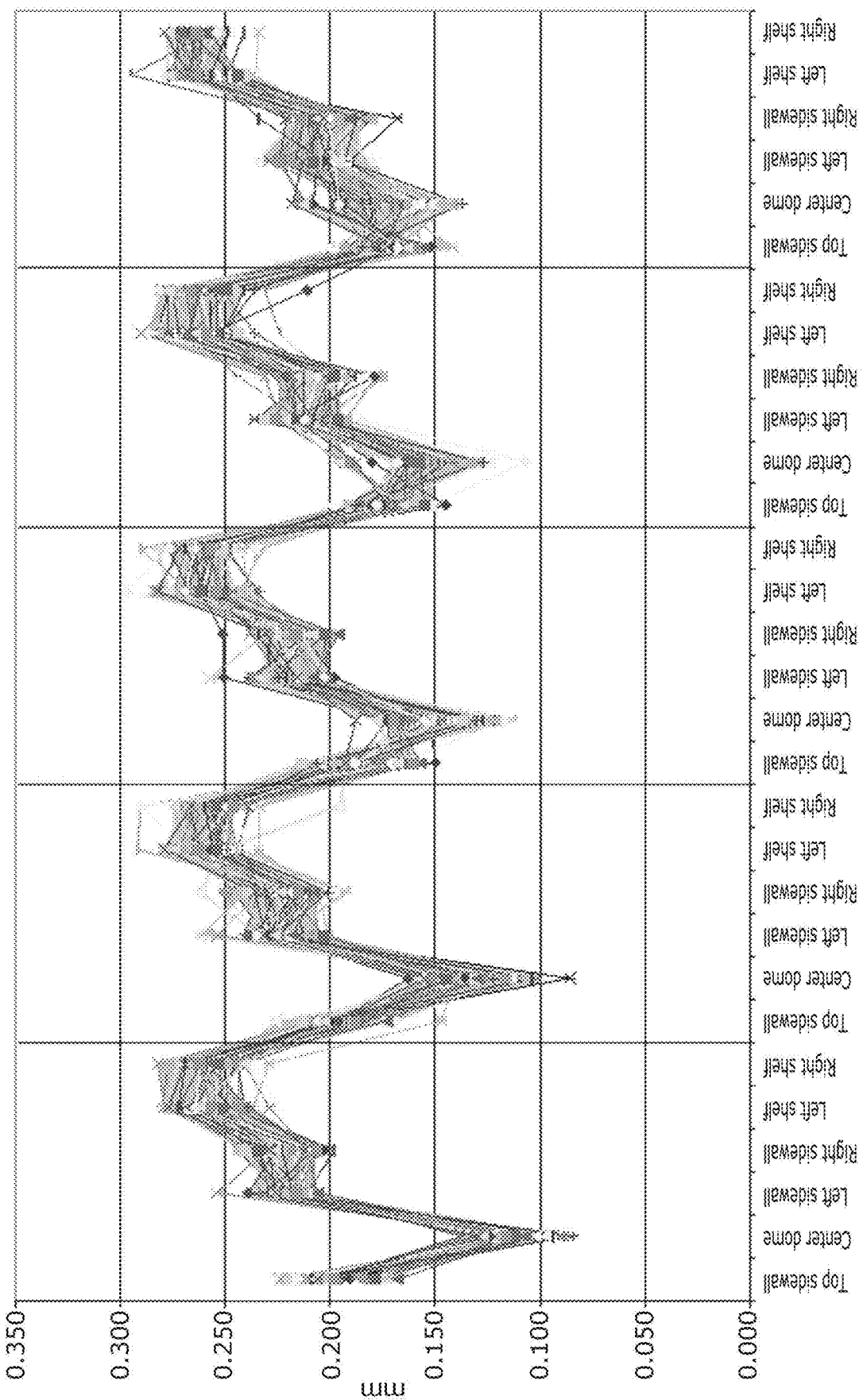
FIG. 14 illustrates a thickness profile of a blister package formed of a tri-layer PVC-ACLAR-PVC material.

FIG. 14 is a graph illustrating thickness at different locations enumerated in FIG. 13 along the cross-section line. The blistered base sheet here is in formed of a tri-layer laminate of PVC-ACLAR-PVC (7.5 mil-3.0 mil-7.5 mil; 0.19 mm-0.07 mm-0.19 mm). The thinnest point in the blistered base sheet is located at the pinnacle of the dome (about 0.175 mm to about 0.075 mm) and the thickest points are located on the shelves (about 0.275 mm to about 0.225 mm).

Figure 15:
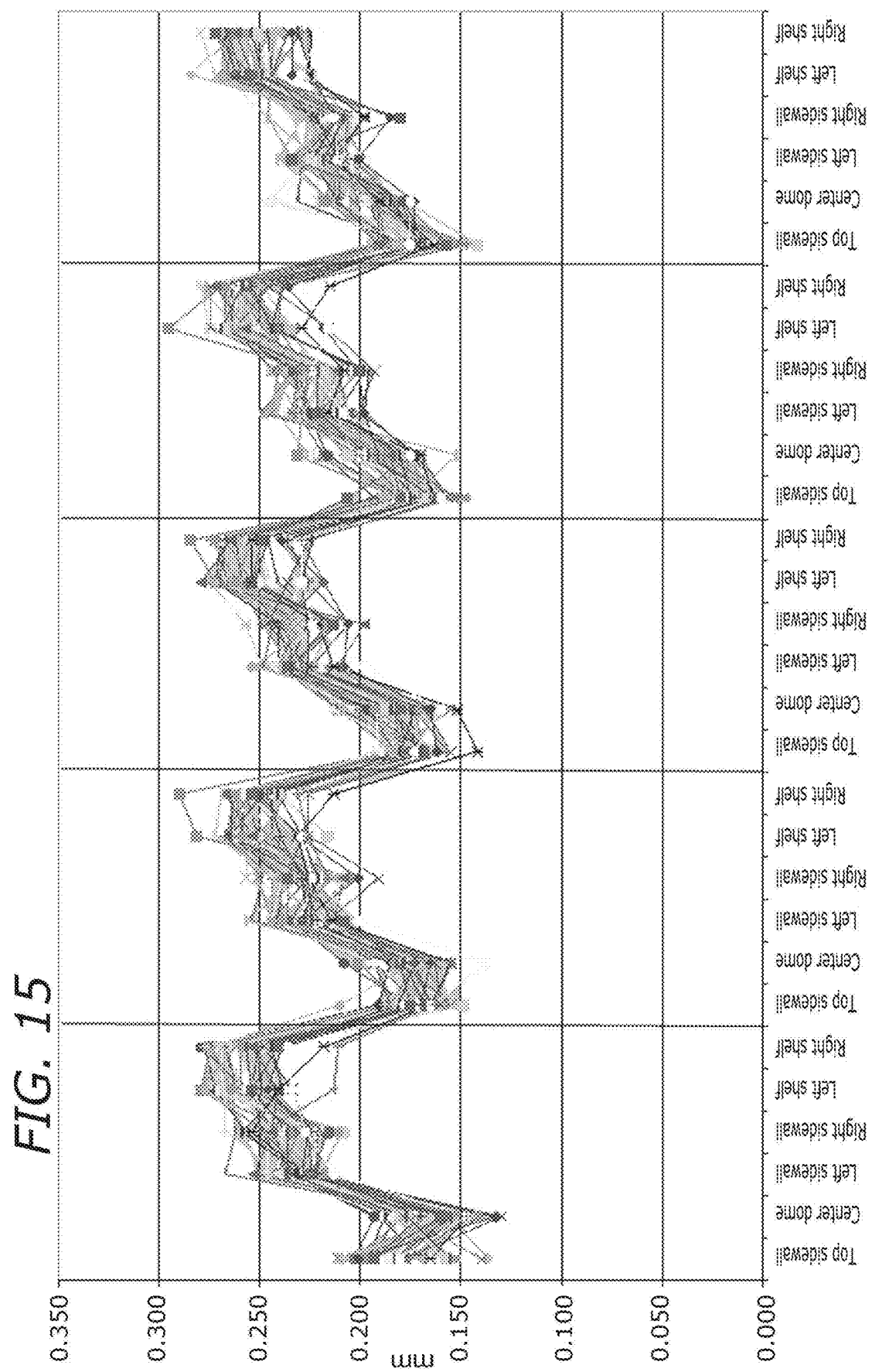
FIG. 15 illustrates a thickness profile of a blister package formed of a bi-layer PVC-ACLAR material.

FIG. 15 is a graph illustrating thickness at different locations enumerated in FIG. 13 along the cross-section line. The blistered base sheet here is in formed of a bi-layer laminate of PVC-ACLAR (15 mil-4.0 mil; 0.38 mm-0.10 mm). The thinnest point in the blistered base sheet is located at the pinnacle of the dome (about 0.187 mm to about 0.125 mm) and the thickest points are located on the shelves (about 0.225 mm to about 0.275 mm).

Figure 16:
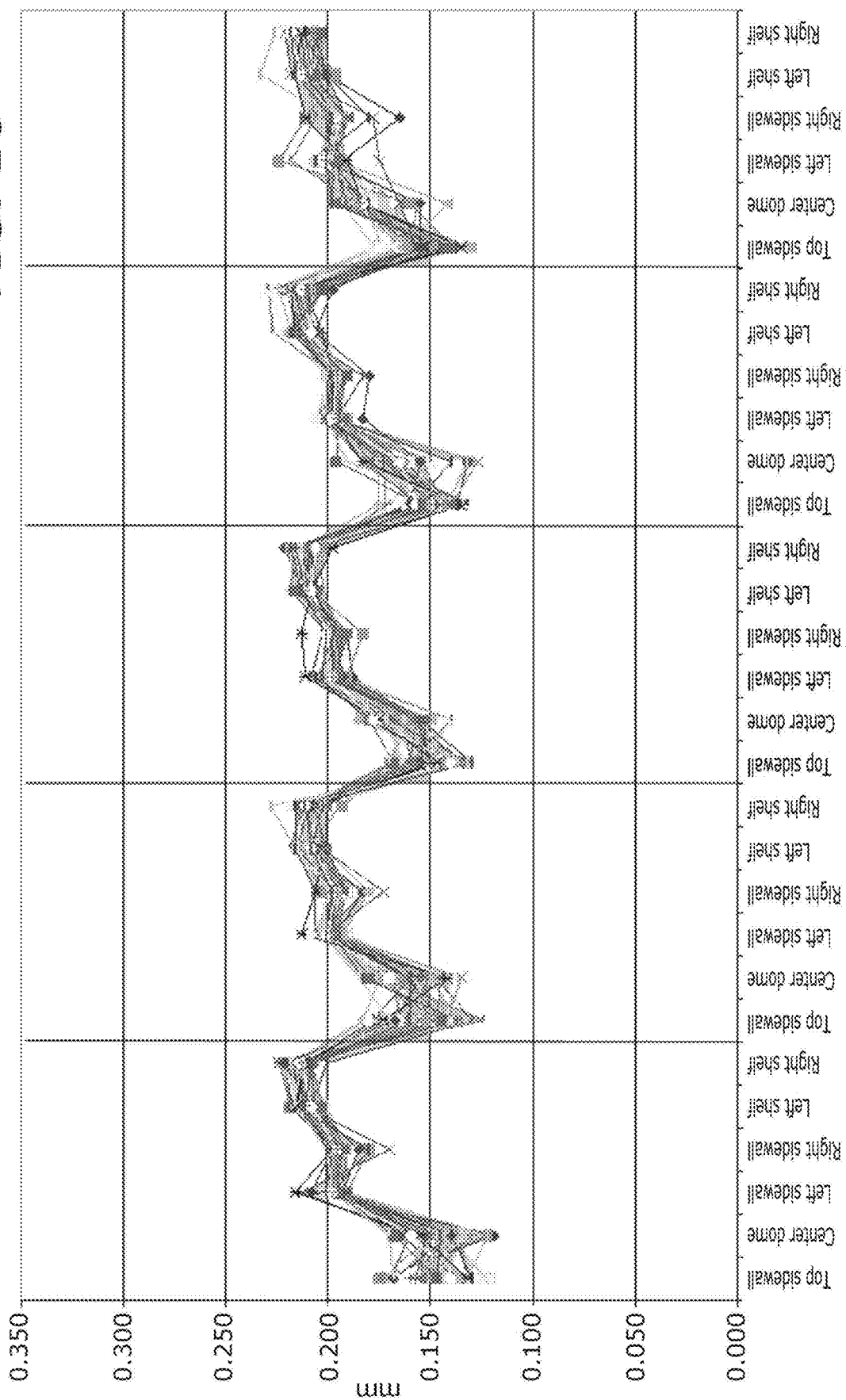
FIG. 16 illustrates a thickness profile of a blister package formed of a bi-layer CoPETG-ACLAR material.

FIG. 16 is a graph illustrating thickness at different locations enumerated in FIG. 13 along the cross-section line. The blistered base sheet here is in formed of a bi-layer laminate of CoPETG-ACLAR (12 mil-4.0 mil; 0.30 mm-0.10 mm). The thinnest point in the blistered base sheet is located at the pinnacle of the dome (about 0.125 mm to about 0.165 mm) and the thickest points are located on the shelves (about 0.200 mm to about 0.275 mm).

Standard deviations for the various measurements from FIGS. 14-16 are illustrated in the graph in FIG. 17. Based on the graphs of FIGS. 14-17, it can be understood by on skilled in the art that the thicknesses of processed blistered base sheets can be reproducible with standard deviations between about 0.004 and about 0.023 mm. Signal to noise on the same samples can range from about 0.020 to about 0.135.

Example 4

Moisture Vapor Permeation

A blistered base sheet with foil overwrap was selected because of moisture vapor permeation characteristics and the ability to form a suitably tight package.

Supplier specifications for moisture vapor permeation characteristics of the blister packaging materials can be less than 0.058 g water/m$^2$/day for a laminated base film, less than 0.01 0 g water/m$^2$/day for a laminated lid and less than 0.010 g water/m$^2$/day for a laminated overwrap when measured according to ASTM F1249 at 37.8° C./90% RH.

A sealed assembly consisting of the blistered base sheet and foil overwrap was individually tested according to ASTM Method F1249—Standard Test Method for Water Vapor Transmission Rate through Plastic Film and Sheeting Using a Modulated Infrared Sensor. Blistered base sheet samples were prepared by injecting 1 cc of water into each blister strip and placing an impermeable epoxy resin over the opening created by syringe. This created a reservoir of water within the blister card. Foil overwrap packages containing nested blister packs were prepared by injecting 1 cc of water into the overwrap and placing an impermeable epoxy resin over the opening created by the syringe. The permeation characteristics were determined by placing a sample into a Mocon Permatran instrument chamber, and flushing the chamber headspace with dry air. Escaping water vapor can diffuse and permeate through sealed test samples and mixes with the gas within the chamber headspace and is carried to an infrared sensor. The infrared sensor measures the fraction of infrared energy absorbed by the water vapor and produces an electrical signal, the amplitude of which is proportional to water vapor concentration. The amplitude of the electrical signal produced by the test samples is then compared to the signal produced by measurement of a calibration film with a known water vapor transmission rate. This information is then used to calculate the rate at which moisture is transmitted through the material being tested. Testing was conducted at 25° C./100% RH.

A sealed blistered base sheet as described herein having a trilaminar layer of ACLAR sandwiched by PVC layers as outer layers exhibits a moisture permeation rate of about 0.00004 g water/blister pack/day, and the sealed assembled overwrap package moisture permeation rate is about 0.040 g water/overwrap pack/day. These low values demonstrate the suitability of the package configuration for cartridges containing pharmaceutical formulations. The package configuration has been confirmed in practice during long term stability studies through testing of TI Powder for moisture content. Data shows no discernable changes in moisture content on stability in either condition (5° C. or 25° C./60% RH), validating the suitability for use of the blister card with foil overwrap package configuration with TECHNOSPHERE® (MannKind Corp., CA) Insulin.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A method of manufacturing a high moisture barrier blister package for a cartridge containing a pharmaceutical formulation comprising a diketopiperazine, comprising:
    creating a blister in an ACLAR base sheet using heat between 120 degrees C. and about 150 degrees C., pressure between about 4 bars and about 7 bars, and a plug,
    wherein each blister includes a dome structure and a shelf having an exterior surface configured to hold the cartridge having a cup and a lid, wherein the shelf includes an indentation in the exterior surface; and further wherein the Water Vapor Transmission Rate of the blister is less than 0.015 grams $H_2O$ per blister per day.

2. The method of claim 1, wherein the creating occurs at a predetermined cycle.

3. The method of claim 2, wherein the predetermined cycle is between 10 cycles per min and about 30 cycles per min.

4. The method of claim 1, further comprising placing the cartridge in the blister.

5. The method of claim 1, further comprising providing a lid material.

6. The method of claim 1, further comprising pulling the lid material and the base sheet together.

7. The method of claim 1, further comprising sealing the lid to the base sheet.

8. The method of claim 1, further comprising die cutting the sealed lid and base sheet to form the blister package.

9. The method of claim 1, wherein the diketopiperazine is bis-3,6-(N-fumaryl-4-aminobutyl)-2,5-diketo-diketopiperazine.

10. The method of claim 1, wherein the pharmaceutical formulation includes a peptide, protein, a small molecule or a nucleic acid.

11. The method of claim 1, wherein the pharmaceutical formulation includes insulin, glucagon like peptide 1, glucagon, oxytocin, oxyntomodulin, peptide YY, sumatriptan, a peptidyl peptidase IV inhibitor, parathyroid hormone, deoxyribonuclease I and active fragments or analogs thereof, neurotransmitter agonist, neurotransmitter antagonists, or a combination thereof.

12. A method of manufacturing a high moisture barrier blister package for a cartridge containing a pharmaceutical formulation comprising an active agent and a diketopiperazine, comprising:
    bonding a film to a blistered ACLAR base sheet,
    wherein cavities are molded on a base sheet comprising at least three layers selected from polyvinyl chloride and fluoropolymer; wherein the cartridge comprises a container and a top and is in the cavities when the film is bonded to the blistered base sheet; and wherein the blistered base sheet is perforated to segment the cavities from one another; and further wherein the Water Vapor Transmission Rate of the blister is less than 0.015 grams $H_2O$ per blister per day.

13. The method of claim 12, wherein the diketopiperazine is bis-3,6-(N-fumaryl-4-aminobutyl)-2,5-diketo-diketopiperazine.

14. The method of claim 12, wherein the active ingredient is a peptide, protein, a small molecule or a nucleic acid.

15. The method of claim 12, wherein the active ingredient is selected from the group consisting of insulin, glucagon like peptide 1, glucagon, oxytocin, oxyntomodulin, peptide YY, sumatriptan, a peptidyl peptidase IV inhibitor, parathyroid hormone, deoxyribonuclease I and active fragments or analogs thereof, neurotransmitter agonist, neurotransmitter antagonists, or a combination thereof.

* * * * *

UNITED STATES PATENT AND TRADEMARK OFFICE
CERTIFICATE OF CORRECTION

Page 1 of 1

PATENT NO. : 12,128,177 B2
APPLICATION NO. : 16/847483
DATED : October 29, 2024
INVENTOR(S) : Bergey It is certified that error appears in the above-identified patent and that said Letters Patent is hereby corrected as shown below:

In the Claims

At Column 10, Lines 17-18, "bis-3,6-(N-fumaryl-4-aminobutyl)-2,5-diketo-diketopiperazine" should be changed to --3,6-bis-(4-fumaryl-aminobutyl)-2,5-diketopiperazine--

At Column 16, Lines 45-46, "bis-3,6-(N-fumaryl-4-aminobutyl)-2,5-diketo-diketopiperazine" should be changed to --3,6-bis-(4-fumaryl-aminobutyl)-2,5-diketopiperazine--

At Column 17, Lines 5-6, "bis-3,6-(N-fumaryl-4-aminobutyl)-2,5-diketo-diketopiperazine" should be changed to --3,6-bis-(4-fumaryl-aminobutyl)-2,5-diketopiperazine--

Signed and Sealed this
Eleventh Day of March, 2025

Coke Morgan Stewart
*Acting Director of the United States Patent and Trademark Office*